United States Patent [19]

Ciurca, Jr. et al.

[11] 4,124,398
[45] Nov. 7, 1978

[54] THIYL BLEACHING AGENTS FOR PHOTOGRAPHIC PROCESSES

[75] Inventors: Samuel J. Ciurca, Jr., Rochester; Carl F. Kohrt, Pittsford, both of N.Y.

[73] Assignee: Eastman Kodak Company, Rochester, N.Y.

[21] Appl. No.: 814,561

[22] Filed: Jul. 11, 1977

[51] Int. Cl.$^2$ .............................................. G03C 1/02
[52] U.S. Cl. .................................................. 96/114.1
[58] Field of Search ........................................ 96/114.1

[56] References Cited

FOREIGN PATENT DOCUMENTS 42,529  1976  Japan ...................................... 96/114.1

Primary Examiner—Mary F. Kelley
Attorney, Agent, or Firm—Arthur H. Rosenstein

[57] ABSTRACT

Disclosed herein are aqueous and nonaqueous photographic bleaching solutions and radiation sensitive elements comprising a thiyl bleaching agent precursor having the formula

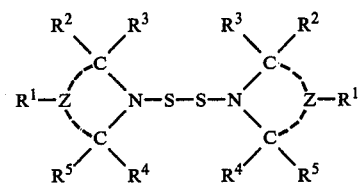

wherein Z comprises the nonmetallic atoms necessary to complete a 5 to 7 member heterocyclic ring; $R^2$, $R^3$, $R^4$ and $R^5$ are independently selected from the group consisting of alkyl, cycloalkyl, aralkyl, aryl or $R^2$ and $R^3$ or $R^4$ and $R^5$ can be taken together with the carbon atom of the ring to which they are attached to form a cycloalkyl or cycloalkenyl group; and $R^1$ is independently selected from the group consisting of hydrogen, oxo and a complexing ligand for silver (I) ion wherein the Ksp of the complexed product of the ligand and silver (I) ion is less than about $10^{-12}$ at 25° C. The thiyl bleaching agents disclosed herein are capable of bleaching preformed or predeveloped metals such as silver in both aqueous and nonaqueous photographic materials. They do not adversely affect the photographic properties of radiation sensitive emulsions and can be thermally activated in a dry photothermographic process.

20 Claims, No Drawings

THIYL BLEACHING AGENTS FOR PHOTOGRAPHIC PROCESSES

BACKGROUND OF THE INVENTION

1. Field of the Invention

The present invention relates to novel compositions and methods for bleaching metals in photographic materials. More particularly, the present invention relates to novel bleaching agents and their use in aqueous and nonaqueous photographic materials. One of its aspects relates to novel bleaching solutions which are capable of bleaching preformed or predeveloped silver in aqueous and nonaqueous photographic materials. Another of its aspects relates to novel bleaching agents for incorporation into radiation sensitive elements, particularly photothermographic elements, for converting metallic image silver in said elements to a colorless product.

2. Description of the Prior Art

In the processing of many photographic silver halide color elements and in some black-and-white photographic processes, it is necessary to remove metallic silver formed during development. This is ordinarily accomplished by the use of a silver bleaching composition which converts metallic silver into a soluble silver salt. A bleach commonly used for this purpose is an aqueous solution of a water-soluble ferricyanide, such as sodium or potassium ferricyanide, and an alkali metal bromide. Aqueous bleaching solutions comprising aromatic nitroso bleaching agents are described in U.S. Pat. Nos. 2,625,477 (Sawdey), issued Jan. 13, 1953; and 2,705,201 (Tulagin), issued Mar. 29, 1955. U.S. Pat. No. 3,707,374 (Van Der Voorn et al.), issued Dec. 26, 1972, relates to aqueous bleaching solutions comprising water-soluble persulfate salts or water-soluble nitrosodiumsulfonate salts and aromatic amines.

Combined bleaching and fixing compositions for use in photography, commonly referred to as bleach-fix compositions, have been known for many years. They are used in processing silver halide photographic materials to simultaneously accomplish the steps of bleaching and fixing and thereby eliminate one step in the conventional processing procedure. The essential components of a bleach-fix composition are the bleaching agent, i.e. an agent which oxidizes the metallic silver in the silver image to a soluble form, and the fixing agent, i.e., an agent which dissolves the undeveloped silver halide and the silver salts formed by the action of the bleaching agent. U.S. Pat. No. 3,189,452 (Bard et al.), issued June 15, 1965, described aqueous bleach-fix compositions prepared by combining conventional bleaching agents such as alkali metal dichromates and alkali metal ferricyanides with conventional fixing agents such as alkali metal thiocyanates. Other known aqueous bleach-fix solutions include those described in U.S. Pat. No. 3,615,508 (Stephen et al.), issued Oct. 26, 1971; U.S. Pat. No. 3,634,088 (Cooley), issued Jan. 11, 1972, wherein the solutions comprise a ferric salt of an aminopolycarboxylic acid as a bleaching agent and a thiosulfate as a fixing agent; U.S. Pat. No. 3,706,561 (Mowrey et al.), issued Dec. 19, 1972, wherein ferric ion-ligand complexes are used as bleaching agents and thiosulfates, thiocyanates, thioethers, or thioureas are used as fixing agents; and U.S. patent application Ser. No. 389,063 (Mowrey), filed Aug. 16, 1973.

U.S. Pat. No. 3,034,893 (Bruenner), issued May 15, 1962, relates to the use of particular disulfide salts in aqueous photographic bleach baths as oxidizing agents and complexing agents for silver ions, rendering the resulting silver complexes water-soluble. U.S. Pat. No. 3,241,966 (Heilmann et al.), issued Mar. 22, 1966, relates to aqueous bleach-fix solutions comprising polyalkylene oxides wherein some of the ether linkages have been replaced by disulfide linkages.

Silver-dye-bleach processes are well known, having been described, for example, in J. S. Friedman, *History of Color Photography*, pages 405–429 (1944) and A. Meyer, *The Journal of Photographic Science*, Vol. 13, pages 90–97, (1965). These processes involve developing a silver halide emulsion containing a bleachable dye, and bleaching the dye in just those areas where the silver has been developed. All of the silver ion is removed or rendered transparent and insensitive to light, leaving a dye image in the areas where no metallic silver was present. Typical silver-dye-bleach elements and processes are disclosed in U.S. Pat. No. 3,414,411 (Michel et al.), issued Dec. 3, 1968 and in U.S. Pat. No. 3,904,918 of Mowrey et al., issued Sept. 9, 1975.

It is also well known to develop a latent image in a photothermographic element using thermal processing. After imagewise exposure, the resulting latent image in the photothermographic element is developed and, in some cases, stabilized, merely by uniformly heating the photothermographic element. Such materials and process are described, for example, in U.S. Pat. No. 3,152,904 (Sorensen et al.), issued Oct. 13, 1964; U.S. Pat. No. 3,301,678 (Humphlett et al.), issued Jan. 31, 1967; U.S. Pat. No. 3,392,020 (Yutzy et al.), issued July 9, 1968; U.S. Pat. No. 3,457,075 (Morgan et al.), issued July 22, 1969; British Pat. No. 1,131,108 published Oct. 23, 1968; German Pat. No. 888,045 issued June 29, 1943 and British Pat. No. 1,161,777 published Aug. 20, 1969. Certain photothermographic materials for producing an image in color are also known as described, for example, in U.S. Pat. No. 3,531,286 (Renfrew), issued Sept. 29, 1970 and U.S. Pat. No. 3,761,270 (deMauriac et al.), issued Sept. 25, 1973.

U.S. application Ser. No. 642,928 of Cerquone et al., filed Dec. 22, 1975 now U.S. Pat. No. 4,021,240 relates to photothermographic and thermographic elements, compositions and processes for providing a developed image in color. There is no teaching or suggestion in this application of the present invention.

Copending U.S. application Ser. No. 662,403 of Mowrey and Oftedahl, filed Mar. 1, 1976 now abandoned relates to an activator sheet for a dry thermal silver dye bleach process. The sheet comprises a support, a diffusible mineral or organic acid and a non-hydrolyzable polymeric vehicle. This application does not teach or suggest the present invention.

Applicants are aware of no prior art which teaches or suggests the present invention. It is an object of this invention to provide bleaching solutions and radiation sensitive elements, particularly photothermographic elements, comprising novel thiyl bleaching agents. These bleaching agents provide the following advantages over the bleaching agents of the prior art:

1. The thiyl bleaching agent precursors may be incorporated in photographic elements without adversely affecting the photographic properties of radiation sensitive emulsions and may be thermally activated;

2. They are capable of bleaching preformed or predeveloped silver in both aqueous and nonaqueous photographic materials;

3. They are effective in converting metallic image silver to a colorless product by a dry thermal process; and 4. They are biodegradable and easily destroyed by ozonolysis, lessening environmental pollution.

Nonaqueous photographic materials used in the practice of the present invention include those in which a radiation sensitive element is contained in a water-insoluble or a water-impermeable binder. Exemplary of these materials are photothermographic elements adapted for dry physical development which contain poly(vinyl butyral) or another suitable binder.

Aqueous photographic materials include those in which a radiation sensitive element is contained in a water-soluble or a water-permeable binder, such as hydrophilic proteinaceous colloids like gelatin. Examples of these materials can be found in *Product Licensing Index*, Vol. 92, December 1971, Publication 9232, pages 107–110, published by Industrial Opportunities Ltd., Homewell, Havant Hampshire, P09 1EF, UK.

SUMMARY OF THE INVENTION

One aspect of the present invention comprises an aqueous or nonaqueous photographic bleaching solution having an effective hydrogen ion concentration greater than about $10^{-7}$ comprising a thiyl bleaching agent precursor having the formula (I):

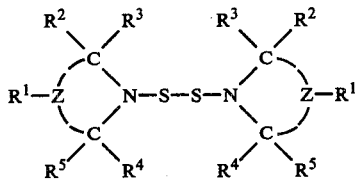

wherein Z comprises the nonmetallic atoms necessary to complete a 5 to 7 member heterocyclic ring; $R^1$ is independently selected from the group consisting of hydrogen, oxo and a complexing ligand for silver (I) ion wherein the Ksp of the complexed product of the ligand and silver (I) ion is less than about $10^{-12}$ at 25° C; and $R^2$, $R^3$, $R^4$ and $R^5$ are independently selected from the groups consisting of substituted or unsubstituted alkyl, preferably having 1 to 6 carbon atoms, cycloalkyl, aralkyl, aryl or $R^2$ and $R^3$ or $R^4$ and $R^5$ can be taken together with the carbon atom of the ring to which they are attached to form a cycloalkyl or cycloalkenyl having from 4 to 10 carbon atoms.

Another aspect comprises an aqueous or nonaqueous photographic bleaching solution having an effective hydrogen ion concentration greater than about $10^{-7}$ comprising a silver (I) ion complexing agent wherein the Ksp of the complexed product of silver (I) ion and the complexing agent is less than about $10^{-12}$ at 25° C; and a thiyl bleaching agent precursor having the formula (I) above.

In another aspect of the present invention, a radiation sensitive element comprises a support having thereon a silver halide emulsion layer and in the same layer a thiyl bleaching agent precursor having the formula (I) above wherein Z comprises the nonmetallic atoms necessary to complete a 5 to 7 member heterocyclic ring; and $R^1$ is independently selected from the group consisting of hydrogen and oxo.

In still another aspect of the present invention, a radiation sensitive element comprises a support having thereon a silver halide emulsion layer; and at least one different layer comprising a silver (I) ion complexing agent wherein the Ksp of the complexed product of silver (I) ion and the complexing agent is less than about $10^{-12}$ at 25° C, and a thiyl bleaching agent precursor having the formula (I) above wherein Z comprises the nonmetallic atoms necessary to complete a 5 to 7 member heterocyclic ring; and $R^1$ is independently selected from the group consisting of hydrogen, oxo and a complexing ligand for silver (I) ion wherein the Ksp of the complexed product of the ligand and silver (I) ion is less than about $10^{-12}$ at 25° C.

In a further aspect of the present invention, a photothermographic element comprises a support having thereon a layer comprising:
 a. a reducing agent;
 b. a silver salt oxidizing agent;
 c. a binder;
 d. a silver halide; and
 e. a thiyl bleaching agent precursor having the formula (I) above wherein Z comprises the nonmetallic atoms necessary to complete a 5 to 7 member heterocyclic ring; and $R^1$ is independently selected from the group consisting of hydrogen and oxo.

Still another aspect of the present invention comprises a photothermographic element comprising a support having thereon a layer comprising:
 a. a reducing agent;
 b. a silver salt oxidizing agent;
 c. a binder; and
 d. a silver halide
and a different layer comprising a silver (I) ion complexing agent wherein the Ksp of the complexed product of silver (I) ion and the complexing agent is less than about $10^{-12}$ at 25° C; and a thiyl bleaching agent precursor having the formula (I) above wherein Z comprises the nonmetallic atoms necessary to complete a 6 member heterocyclic ring; and $R^1$ is independently selected from the group consisting of hydrogen, oxo and a complexing ligand for silver (I) ion wherein the Ksp of the complexed product of the ligand and silver (I) ion is less than about $10^{-12}$ at 25° C.

In still another aspect of the present invention a process for bleaching a metal having a standard electrode potential at 25° C of 0.799 or less in a photographic element comprising a support having thereon a layer comprising a metal having a standard electrode potential at 25° C of 0.799 or less, comprises immersing the element in a photographic bleaching solution having a pH less than about 7.0 comprising a solvent and the thiyl bleaching agent precursor described herein.

Still another aspect of the present invention comprises a process for producing a photographic image comprising the steps of (1) exposure of an improved photothermographic element to light, said element comprising a support having thereon a layer comprising a reducing agent; a silver salt oxidizing agent; a binder; and a silver halide; and (2) thermal development at a temperature above about 80° C, the improvement comprising incorporation into the photothermographic element, a thiyl bleaching agent precursor having the formula (I) above wherein Z comprises the nonmetallic atoms necessary to complete a 5 to 7 member heterocyclic ring; and $R^1$ is independently selected from the group consisting of hydrogen, oxo and a complexing ligand for silver (I) ion wherein the Ksp of the complexed product of the ligand and silver (I) ion is less than about $10^{-12}$ at 25° C.

DESCRIPTION OF THE PREFERRED EMBODIMENTS

In all aspects of the present invention, Z of formula (I) represents the nonmetallic atoms, such as C, N, O, S and the like, necessary to complete a 5 to 7 member heterocyclic ring, such as pyrrolidine, piperidine, and the like, and isomers thereof. The heterocyclic ring may be saturated or unsaturated. $R^1$ is selected from the group consisting of hydrogen, oxo and a complexing ligand, as defined hereinabove, such as

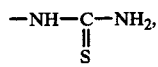

—SCN and the like or a precursor to a complexing ligand such as the isothiouroniums disclosed in U.S. Pat. No. 3,531,285 of Haist et al., issued Sept. 29, 1970. In addition to $R^1$, the heterocyclic ring may be substituted with one or more substituents independently selected from the group consisting of alkyl having from 1 to 20 carbon atoms, such as methyl, ethyl, propyl, butyl, decyl, octadecyl, eicosyl and the like and isomers thereof and preferably alkyl; alkoxy having from 1 to 20 carbon atoms, such as methoxy, ethoxy, propoxy, butoxy and the like; cycloalkyl having from 5 to 7 carbon atoms, such as cyclopentyl, cyclohexyl, cycloheptyl and the like; aryl having from 6 to 10 carbon atoms, such as phenyl, naphthyl and the like; and heterocyclic rings having from 1 to 3 nonmetallic atoms, such as morpholino, triazione, and the like.

It is believed that the thiyl bleaching agent precursors described herein form free radical thiyl compounds during thermal development at temperatures greater than about 100° C. The formation of thiyl compound is thought to occur according to the following formula:

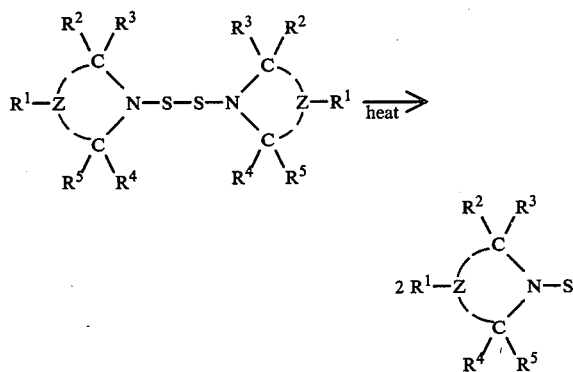

In a preferred embodiment of the present invention, a photographic bleaching solution having an effective hydrogen ion concentration greater than about $10^{-7}$ comprises a thiyl bleaching agent precursor described hereinabove wherein Z comprises the nonmetallic atoms necessary to complete a 6 member heterocyclic ring, such as piperidine, isoxazine, and the like; $R^1$ is as defined above; and $R^2$, $R^3$, $R^4$ and $R^5$ are methyl.

A more preferred embodiment of the present invention comprises a photographic bleaching solution described hereinabove comprising a thiyl bleaching agent precursor having the formula:

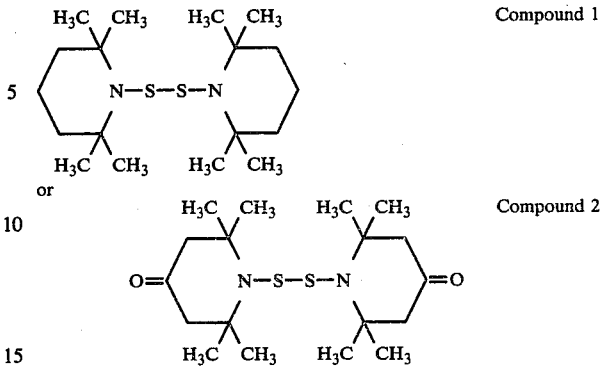

Each thiyl bleaching agent precursor useful in the present invention undergoes decomposition to thiyl radicals at the temperature at which the thiyl bleaching agent precursor melts.

The concentration range of the thiyl bleaching agent precursors useful in the bleaching solutions of the present invention is from about 0.01 M up to the saturated amount limited by the solubility of the particular precursor in the particular solvent, but preferably from about 0.05 M to about 0.25 M. One mole of a thiyl precursor in solution is capable of bleaching up to about 2 moles of silver.

The thiyl bleaching agents which are most useful in the aqueous bleaching solutions of the present invention include Compound 1 and Compound 2. The nonaqueous bleaching solutions of the present invention comprise an organic solvent which can be any of methanol, ethanol, toluene, methylene chloride, acetone etc., and preferably methanol. Both aqueous and nonaqueous bleaching solutions of the present invention tend to be colorless and leave no stain on bleached elements.

The bleaching solutions described herein are preferably used at any "effective" hydrogen ion concentration greater than about $10^{-7}$. By "effective" is meant hydrogen ion concentration (HIC) determined in both nonaqueous and aqueous solutions with Pt electrodes at 23° C by measuring with a commercial pH meter (Corning) vs. a standard calomel electrode. The most useful HIC ranges of the bleaching solutions comprising particular thiyl bleaching agent precursors depend upon the presence or absence of a bleach accelerator or catalyst. In the absence of a catalyst, the most useful HIC range of an aqueous solution may be $10^{-4}$ or greater at 25° C. With a catalyst present, aqueous bleaching solutions are most useful at any HIC greater than about $10^{-7}$ at 25° C. For the nonaqueous bleaching solutions of the present invention, the most useful HIC range is about $10^{-1}$ to about $10^{-4}$ without a catalyst and more than about $10^{-7}$ with a catalyst.

Bleach accelerators or catalysts useful in the practice of this invention include aminophenols, such as

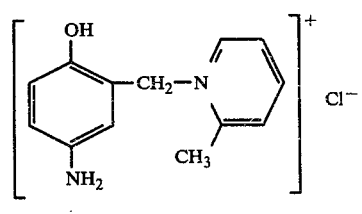

p-aminophenol, p-methylaminophenol, p-dimethylaminophenol, 2,4-diaminophenol and the like; phenylenediamines, such as p-phenylenediamine, N-methyl-p-phenylenediamine, N,N'-dimethyl-p-phenylenediamine, and similar compounds which are capable of forming reactive free radical intermediates, such as semiquinones and the like as disclosed in U.S. Pat. No. 3,707,814; N,N,N',N'-tetramethyl-p-phenylenediamine, 2-methyl-4-diethylamino-aniline, and the like as disclosed in U.S. Pat. No. 3,707,374 (Van Der Voorn et al.), issued Dec. 26, 1972; thiourea; and mercaptothiadiazoles. Electron transfer agent known to be useful as catalysts in silver dye bleach processes, such as phenazine and its derivatives and thiazine derivatives, including quinoxaline, can also be useful in the bleaching solutions of the present invention. Quaternary salts, such as tetrabutylammonium bromide and strong electron acceptors, such as 2,3-dicyano-5,6-dichlorobenzoquinone and tetracyanoethylene are particularly useful in nonaqueous bleaching solutions.

The amount of a catalyst useful in the bleaching solutions of the present invention depends upon such circumstances as the type of catalyst and bleaching agent precursor employed, the pH, the solvent, the hydrophobic and hydrophilic nature of a radiation sensitive element to be bleached, the amount of silver to be removed, etc. The concentration range is normally from zero up to the molar amount of thiyl bleaching agent precursor used, and preferably about 0.005 M.

As noted hereinabove, the bleaching solutions of the present invention may comprise a silver (I) ion complexing agent wherein the Ksp of the complexed product of silver (I) ion and the complexing agent is less than about $10^{-12}$ at 25° C. Suitable complexing agents include such compounds as

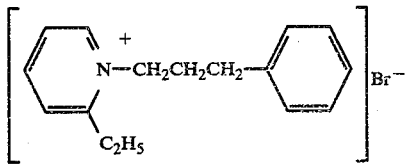

and other onium halides, ammonium thiosulfate, sodium thiocyanate and thiourea. These complexing agents are advantageously incorporated in the bleaching solutions when the particular thiyl bleaching agent precursors used may have adverse sensitometric effects on the radiation sensitive properties of radiation sensitive elements to be bleached.

In addition to the thiyl bleaching agent precursor, addenda commonly used in photographic bleaching solutions can be incorporated in the bleaching solutions of this invention. For example, the solutions can advantageously contain alkali metal halides or ammonium halides, such as sodium bromide, potassium bromide, ammonium bromide, sodium chloride, potassium chloride, ammonium chloride; mercaptotriazoles; and thiocyanates which function to aid in the bleaching; non-chelated salts of aminocarboxylic acids which function as sequestering agents, such as sodium salts of ethylenediaminetetraacetic acid; hardeners, such as aldehydes; and the like. It is advantageous to also incorporate a buffer in the bleaching solution to provide proper pH control. For this purpose, any of the buffers commonly used in photographic processing solutions may be employed, e.g., phosphoric acid, hydrochloric acid, alkali metal phosphates, acetic acid, alkali metal acetates, maleic acid, alkali metal maleates, alkali metal borates, etc., and preferably those buffers having anions capable of forming sparingly soluble salts with silver (I) ion.

The thiyl bleaching agent precursors described herein may be useful in combination with one or more other bleaching agents including other thiyl precursors; conventional inorganic bleaching agents such as ammonium ferricyanide, ferric chloride and the like; and organic oxidants such as ammonium persulfate, 2,2,6,6-tetramethyl-4-oxypiperidine and the like.

The bleaching solutions of the present invention can be used as bleach-fix solutions whereby bleaching and fixing of a radiation sensitive element are accomplished in one step of processing. Thiyl bleaching agent precursors which also act as fixing agents include those wherein R is —S—C|N,

and the like. Other thiyl agent precursors may be used with conventional fixing agents which include alkali thiocyanates, such as sodium thiocyanate, potassium thiocyanate, and the like; ammonium thiocyanate; alkali metal thiosulfates, such as sodium thiosulfate; thioureas; alkali metal selenocyanates, such as sodium selenocyanate, potassium selenocyanate and the like; pyridinium salts; and carboxylic acid. The fixing agent is usually present in a concentration range of about 0.01 M to about 1.0 M in the bleach-fix solution. Bleach-fix solutions of the present invention advantageously comprise sulfurization retardants such as carbonyl bisulfite adducts, including alkali metal bisulfites, alkaline earth metal bisulfites, and amine bisulfites. Exemplary of such adducts are sodium acetaldehyde bisulfite, sodium propionaldehyde bisulfite, succinaldehyde bis-sodium bisulfite, sodium acetone bisulfite, and the like.

The bleaching solutions of the present invention can be used in a process to bleach any metal in radiation sensitive elements which has a standard electrode potential, as measured at 25° C. of about 0.799 or less. Exemplary of such metals are silver, iron, copper and the like. The bleaching process comprises immersing an element comprising at least one of such metals in a photographic bleaching solution of the present invention and leaving it in said solution, for example, for a time of about 0.5 to about 20 minutes. Aqueous bleaching solutions of the present invention are effective at any conventional processing temperature used in the art. A suitable processing temperature for nonaqueous solutions is dependent on the boiling point of the organic solvent employed and can range up to about 140° C. Bleaching of radiation sensitive elements can be done before or after exposure to actinic radiation and before or after image development.

The bleaching and bleach-fix solutions of the present invention can be used in the processing of radiation sensitive elements designed for black-and-white processing, reversal color processing or in the processing of negative color elements or color print materials. They can be employed with radiation sensitive elements which are processed in color developers containing couplers or with elements which contain the coupler in the silver halide emulsion layers or in layers contiguous thereto.

The thiyl precursors can be incorporated in radiation sensitive elements wherein it is desired to bleach any metal which has a standard electrode potential of about 0.799 or less at 25° C. Preferably such elements include photographic siler halide elements which can be panchromatic or orthochromatic. They can take the form of radiographic elements, direct-positive elements, negative image-forming elements, thermally processable elements, image transfer elements, multicolor elements, high contrast elements, silver dye bleach materials and the like. The thiyl bleaching agent precursors are present in the radiation sensitive elements of the present invention in a concentration within the range of about 0.5 mole/mole of silver to about 10 mole/mole of silver, and preferably within the range of from about 1.0 to about 3.0 mole/mole of silver.

The silver (I) ion complexing agents useful in the present invention wherein the Ksp of the complexed product of silver (I) ion and the complexing agent is less than about $10^{-12}$ at 25° C. are the same as those described above as useful in the bleaching solutions of the present invention. The Ksp value in radiation sensitive elements is taken to be the same as that measured in solution by techniques known in the art, such as disclosed by J. N. Butler in *Solubility and pH Calculations*, Addison-Wesley Publishing, 1964, hereby incorporated by reference.

Some of the thiyl precursors described herein can be mixed with a silver halide emulsion and coated together in the same layer. Such precursors, including Compound 1 and Compound 2 do not interfere with either exposure, image development or color-forming reactions, if any. Following processing, the bleaching agent formed from the precursor can be made to selectively bleach the silver halide image when released from a precursor or by introducing a suitable complexing agent which has a complexing ligand for silver (I) ion. This complexing agent suppresses the concentration of silver (I) ion thereby promoting the bleaching of silver meta. Thiyl bleaching agent precursors having complexing ligands may cause desensitization of the silver halide emulsion and hence cannot be incorporated in the emulsion. They may be coated as interlayers or overcoats such that image development is completed before the bleaching agents can diffuse into the image layers.

The radiation sensitive elements of the present invention comprise supports which can be made of a variety of materials including polyethylene terephthalate, cellulose acetate butyrate, polycarbonates, polystyrene, polyolefins (e.g., polyethylene, polypropylene) and the like, metals, glass, paper, polyolefin coated paper such as polyethylene or polypropylene coated paper which can be pigmented, with $TiO_2$, for example, and electron bombarded to promote emulsion adhesion, and other materials known to those having skill in the art.

The silver halide emulsion layers present in the radiation sensitive elements of the present invention can contain any of the conventional silver halides as the radiation sensitive material, for example, silver chloride, silver bromide, silver bromoiodide, silver chlorobromide, silver chloroiodide, silver iodide, silver chlorobromoiodide, mixtures thereof, and other radiation sensitive silver compounds. Each layer typically contains from about $3 \times 10^{-3}$ moles silver halide/m² to about $2 \times 10^{-2}$ moles silver halide/m² of support.

These layers can also contain additional additives, particularly those known to be beneficial in photographic emulsions, including, for example, stabilizers or antifoggants, particularly the water-soluble inorganic acid salts of cadmium, cobalt, manganese and zinc as disclosed in U.S. Pat. No. 2,829,404, the substituted triazaindolizines as disclosed in U.S. Pat. Nos. 2,444,605 and 2,444,607, speed increasing materials, absorbing dyes, hardeners, plasticizers, and the like. Sensitizers which give particularly good results in the photographic compositions disclosed herein are the alkylene oxide polymers which can be employed alone or in combination with other materials, such as quaternary ammonium salts, as disclosed in U.S. Pat. No. 2,886,437 or with mercury compounds and nitrogen containing compounds, as disclosed in U.S. Pat. No. 2,751,299.

A detailed description of various emulsions in which the thiyl bleach agent precursors can be used can be found in *Product Licensing Index*, Publication No. 9232, December 1971, pages 107–110, published by Industrial Opportunities Ltd., Homewell, Havant Hampshire, PO9 1EF, UK, hereby incorporated by reference.

Thiyl bleaching agent precursors are useful in radiation sensitive elements which are processed by heat. Such elements, as disclosed in U.S. Pat. No. 3,301,678 (Humphlett et al.), issued Jan. 31, 1967, comprise a silver halide emulsion and a development activator and/or alkali release agent which is different from the developing agent or developing agent precursor or stabilizer precursor, and are heat processed at temperatures from about 90° C. to about 210° L C. U.S. Pat. No. 3,669,670 (Haist et al.), issued June 13, 1972, discloses similar elements comprising a silver halide emulsion and certain bis-isothiuronium compounds having an intermediate ureylene or ether moiety which provide, upon heating from about 90° C. to about 250° C., activation of a developing agent present and/or stabilization of a developed image. S-carbamoyl silver salt stabilizer precursors useful in heat processable radiation sensitive elements and compositions for image stabilization are disclosed in U.S. Pat. No. 3,824,103 (Pierce et al), issued July 16, 1974.

Some radiation sensitive elements which can comprise thiyl bleaching agent precursors are known as silver-dye-bleach elements which contain bleachable dyes, preferably nondiffusible dyes, of the type well known in the art.

Conventional photographic developers and dye formers are operable in this invention. These developers can be incorporated in emulsions in accordance with prior art procedures, or can be added to the alkaline processing solution.

Conventional negative developers which are useful include hydroquinones; catechols; aminophenols, such as p-aminophenol and the like; ascorbic acid and its derivatives; reductones, such as phenidone and the like; phenylenediamines, such as p-phenylenediamine, N-methyl-p-phenylenediamine and the like; and combinations thereof. The developers can be in the silver halide emulsion layer or in another suitable location in the element. They can be added from suitable solvents or in the form of dispersions as described in U.S. Pat. NO. 2,592,386 (Yackel), issued Apr. 8, 1952.

Typical hardeners useful in the radiation sensitive elements of the present invention include aldehydes, such as formaldehyde, acetaldehyde and the like; bis(vinyl sulfonyl) compounds; mucochloric acid and the like, aziridine hardeners which are derivatives of dioxane, oxypolysaccharides such as oxystarch, oxy plant gums and the like. Useful concentrations of hardeners are related to the amount of a binder used and are known to those having skill in the art. Typically they are present in a concentration of from about 1.5% by weight to about 5% by weight of the coating solution.

Binders which are useful in the elements of the present invention include colloids, such as gelatin, protein derivatives, e.g., carboxymethylated proteins, colloidal albumin, cellulose derivatives, snythetic resins such as polyvinyl compounds, and the like. Typically, a binder comprises from about 1.0 to about 10.0 weight percent of the emulsion.

In a preferred embodiment of the present invention, the thiyl precursors described hereinabove are incorporated into photothermographic elements. Precursors having $R^1$ substituents selected from the group consisting of hydrogen and oxo can be incorporated into silver halide emulsion layers. Other precursors, particularly those having complexing ligands described hereinabove must be incorporated in layers other than silver halide emulsion layers.

Various reducing agents can be employed in the described photothermographic materials of this invention. These are typically silver halide developing agents and include, for example, polyhydroxybenzenes such as hydroquinone developing agents including, for instance, hydroquinone, alkyl substituted hydroquinones, exemplified by tertiary butyl hydroquinone, methyl hydroquinone, 2,5-dimethyl hydroquinone and 2,6-dimethyl hydroquinone; catechols and pyrogallol; halo-substituted hydroquinones such as chlorohydroquinone or dichlorohydroquinone; alkoxy-substituted hydroquinones such as methoxy hydroquinone or ethoxy hydroquinone and the like. Other reducing agents which can be employed include reductone developing agents such as anhydro dihydro piperidino hexose reductone; hydroxy tetronic acid reducing agents and hydroxy tetronimide developing agents; 3-pyrazolidone developing agents such as 1-phenyl-3-pyrazolidone and 4-methyl-4-hydroxymethyl-1-phenyl-3-pyrazolidone and those described in British Pat. No. 930,572 published July 3, 1963; certain hydroxyl amine developing agents; ascorbic acid developing agents such as ascorbic acid, ascorbic acid ketals, and other ascorbic acid derivatives; phenylenediamine developing agents; certain aminophenol developing agents and the like; bis-β-naphthols, such as 1,1'-bis-β-naphthol, 1,1'-bis-2-naphthol and the like. Combinations of reducing agents can also be employed. A suitable reducing agent is one which provides a developed image within about 90 seconds at a temperature of about 100° to 250° C.pon heating the photothermographic element containing the reducing agent.

Color developers which are useful in this invention are those which, in their oxidized form, are capable of reacting with photographic couplers to form dyes or leuco dyes. Typical useful color developers include sulfonamidophenols and sulfonamidoanilines which can be represented by the structure:

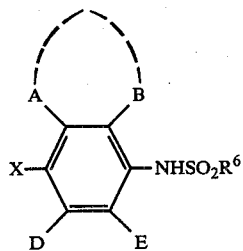

wherein X is —OH or $NR^7R^8$ where $R^7$ and $R^8$ can be the same or different and are chosen from hydrogen, alkyl, aryl or heteryl; $R^6$ can be substituted or unsubstituted aryl, alkyl or heteryl; A, B, D, and E represent substituted or unsubstituted aryl, alkyl, or heteryl, halogen, cyano, hydrogen and the like; additionally, A and B can be taken together to form a fused carbocyclic or heterocyclic ring.

Examples of such useful color developers are sulfonamidophenols and sulfonamidoanilines which have the structures:

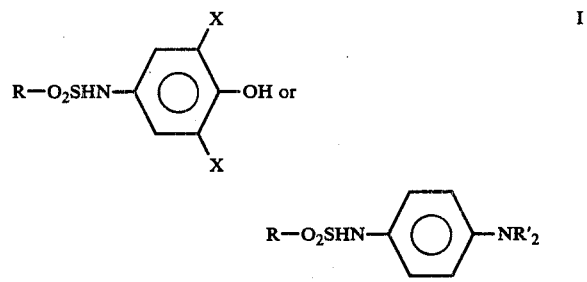

wherein R' is hydrogen or alkyl such as methyl, X is Cl or Br and R is a group which does not adversely affect the desired sensitometric and dye-forming capabilities of the described photothermographic and thermographic element or composition. Typical non-limiting examples of R include alkyl, alkaryl and aralkyl groups, which can contain from 1 to 35 or more carbon atoms in their "alkyl" portions, dialkylamino groups, preferably having alkyl groups of 1 to 8 carbon atoms, heterocyclic groups, aryl groups and the like. Actually, the particular nature of R in such dibromo or dichloro sulfonamidophenol and sulfonamidoaniline compounds of the structures above is not believed critical with respect to the successful practice of this invention, so long as R is not detrimental, as indicated above.

Typical specific examples of the 2,6-dichloro and 2,6-dibromo compounds that have been found to perform well in photothermographic elements, as described above, include:

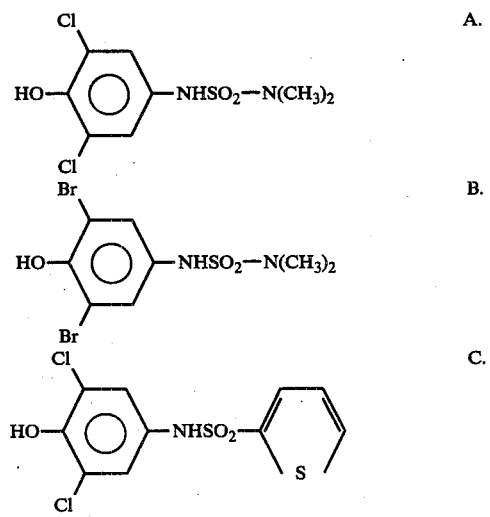

-continued

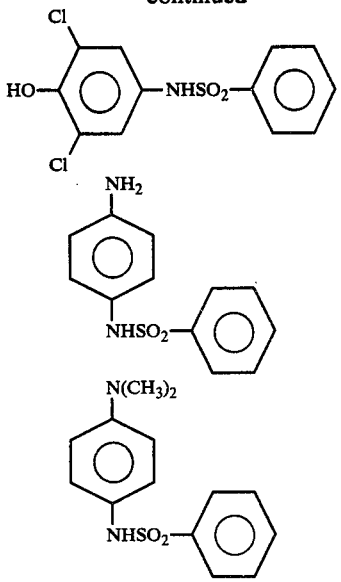

D.

E.

F.

Other reducing agents which are not sulfonamidophenol or sulfonamidoaniline reducing agents and which do not adversely affect the desired color image in the photothermographic material can be used in combination with the other described components of the photothermographic elements and compositions of this invention. Other useful reducing agents include, for example, p-phenylenediamines; and bis-β-naphthol reducing agents as described in U.S. Pat. No. 3,751,249 of Hiller, issued Aug. 7, 1973. Combinations of the described reducing agents can be employed if desired.

Other reducing agents which can be useful with the described 2,6-dichloro and 2,6-dibromo-4-substituted sulfonamidophenol reducing agents are phenolic (leuco base) dye reducing agents. Useful leuco base dye reducing agents are described in U.S. Pat. No. 3,985,565 of Gabrielsen et al, issued Oct. 12, 1976.

The phenolic (leuco base) dye reducing agent(s) react(s) with the silver salt oxidizing agent in the photothermographic element of this invention to produce a desired dye in the imagewise exposed areas of the photothermographic element. It is believed that the latent image silver produced upon imagewise exposure catalyzes the reaction between the reducing agent and the silver salt oxidizing agents. In the case of a thermographic material, the color image is provided by imagewise heating. The described reducing agent is believed to be oxidized imagewise to a dye in the exposed or specifically heated areas.

Examples of useful phenolic (leuco base) dye reducing agents are as follows: 2-(3,5-di-tert-butyl-4-hydroxyphenyl)-4,5-diphenylimidazole, 2-(4-hydroxy-3,5-dimethoxy)-4,5-bis(p-methoxyphenyl)imidazole and bis-(3,5-di-tert-butyl-4-hydroxphenyl)phenylmethane.

Such leuco base dye reducing agents can be prepared by methods known in the art. For example, one method of preparing such reducing agents is described in U.S. Pat. No. 3,297,710 of Silversmith, issued Jan. 10, 1967.

Typical useful concentrations of a reducing agent in the photothermographic elements of the present invention are within the range of from about 0.01 to about 0.10 mole of the described reducing agent per mole of silver ion which corresponds to about 0.1 to about 5.0 millimole of reducing agent per square meter of support.

A typical concentration range of photographic silver halide in the photothermographic elements of this invention is from about 0.005 to about 0.50 mole of photographic silver halide per mole of silver salt oxidizing agent in the described photothermographic elements. In a photothermographic element of the invention, the concentration of photosensitive silver halide is typically within the range of from about $0.02 \times 10^{-2}$ to about $1.0 \times 10^{-2}$ moles of silver halide per square meter of support. Examples of useful photographic silver halides are silver chloride, silver bromide, silver bromoiodide, silver chlorobromoiodide, silver iodide or mixtures thereof and others described hereinabove for radiation sensitive elements. The photographic silver halide is typically present with the other components of the described photothermographic elements in the form of an emulsion which is dispersion of the photographic silver halide in a suitable binder. The photographic silver halide can be coarse or fine-grain, very fine-grain silver halide being especially useful. A composition containing the photographic silver halide can be prepared by any of the well-known procedures in the photographic art, such as single-jet emulsions, Lippmann emulsions, ammoniacal emulsions, thiocyanate or thioether ripened emulsions such as described in U.S. Pat. Nos. 2,222,264 (Nietz et al.), issued Nov. 14, 1940; 3,320,069 (Illingsworth), issued May 15, 1967 and 3,271,157 (McBride), issued Sept. 6, 1966. Surface image photographic silver halide emulsions can be used if desired. If desired, mixtures of surface and internal image photographic silver halide emulsions can be used as described in U.S. Pat. No. 2,996,332 (Luckey et al.), issued Apr. 15, 1961. Negative type emulsions can be used. The silver halide can be a regular grain silver halide such as described in Klein and Moisar, *Journal of Photographic Science*, Volume 12, No. 5, September–October (1964), pages 242–251.

The described silver halide can be unwashed or washed to remove soluble salts. In the latter case, the soluble salts can be removed by chill setting and leaching or an emulsion containing the silver halide can be coagulation washed.

The described silver halide can be sensitized with chemical sensitizers such as with reducing agents; sulfur, selenium or tellurium compounds; gold, platinum or palladium compounds; or combinations of these. Suitable procedures for chemical sensitization are described, for example, in U.S. Pat. Nos. 1,623,499 (Shepard), issued Apr. 5, 1972; 2,399,083 (Waller et al.), issued Apr. 23, 1946; 3,297,447 (McVeigh), issued Jan. 10, 1967 and 3,297,446 (Dunn), issued Jan. 10, 1967.

Photographic silver halide, as described herein, can be protected against loss of sensitivity during keeping. Useful antifoggants and stabilizers which can be used alone or in combination include, for example, thiazolium salts; azaindene; and mercury salts as described, for example, in U.S. Pat. No. 2,728,663 (Allen et al.), issued Dec. 27, 1955; urazoles; sulfocatechols; oximes described, for example, in British Pat. No. 623,448; nitron; nitroindazoles; polyvalent metal salts described, for example, in U.S. Pat. No. 2,839,405 (Jones), issued June 17, 1958; platinum, palladium and gold salts described, for example, in U.S. Pat. No. 2,566,263 (Trivelli et al.), issued Aug. 28, 1951 and U.S. Pat. No. 2,597,915 (Yutzy et al.), issued May 27, 1952.

If desired, the photographic silver halide can be prepared in situ in the photothermographic elements of the present invention. The photographic silver halide can be prepared in a mixture of one or more of the other components of the described photothermographic element rather than prepared separate from the described components and then admixed with them. Such a method is described, for example, in U.S. Pat. No. 3,457,075 (Morgan et al.), issued July 22, 1969. For example, the photographic silver halide can be prepared with a silver salt oxidizing agent such as a silver salt of a fatty acid prior to admixture of the photographic silver halide and silver salt of a fatty acid to other components of the photothermographic materials as described. In this preparation, a halide salt can be added to a suspension of the silver salt of a fatty acid to form a desired photographic silver halide. A useful reaction medium includes water or other solvents which do not interfere with the desired reaction.

The described photothermographic elements comprise a source of silver (I) ion, which is believed to be an oxidizing agent which reacts with the described reducing agent. This silver salt oxidizing agent should be resistant to darkening under illumination to prevent undesired deterioration of a developed image. Preferably, the silver salt oxidizing agent is a long-chain fatty acid. "Long chain" as employed herein is intended to mean a chain of carbon atoms containing at least 10 carbon atoms, typically 10 to 30 carbon atoms. An especially useful class of silver salt oxidizing agents is the silver salts of long-chain fatty acids containing at least 20 carbon atoms. Compounds which are useful silver salts of long-chain fatty acids are, for example, silver behenate, silver stearate, silver oleate, silver laurate, silver hydroxystearate, silver caprate, silver myristate, silver palmitate, and the like.

Other silver salt oxidizing agents which are useful in the present invention include silver benzoate, silver phthalate, silver acetate, silver acid phthalate and the like; silver phthalazinone, silver benzotriazole, silver saccharin and the like; and silver salts of thione compounds, such as those described in U.S. Pat. No. 3,785,830 (Sullivan et al.), issued Jan. 15, 1974, including 3-(2-carboxyethyl)-4-methyl-4-thiazoline-2-thione; 3-(2-carboxyethyl)benzothiazoline-2-thione; 3-(2-carboxyethyl)-5-phenyl-1,3,4-oxadiazoline-2-thione, and the like. Combinations of silver salt oxidizing agents can be used if desired.

In the photothermographic elements of the present invention, the concentration of silver salt oxidizing agent is typically within the range of from about 0.1 to about 100 moles per mole of silver halide, or from about $2 \times 10^{-5}$ to about $2 \times 10^{-2}$ moles of silver salt of a fatty acid per square meter of support.

Minor proportions of oxidizing agents which are not silver salts can be used with the silver salts, if desired, such as zinc oxide, gold stearate, mercury behenate, gold behenate and the like.

It is typically useful to have a long-chain fatty acid present in the described photothermographic material to provide a desired image. For example, when silver behenate is employed as the long-chain fatty acid silver salt, it is typically desirable to have some behenic acid present to provide an improved image. A typical concentration of fatty acid is about 0.1 moles to about 2.0 moles of the fatty acid per mole of silver salt of long-chain fatty acids in the photothermographic element.

A photothermographic element as described can contain various synthetic polymeric binders alone or in combination as vehicles or binding agents and in various layers. Suitable materials are typically hydrophobic, but hydrophilic materials can be useful. They are transparent or translucent and include such substances as cellulose derivatives and synthetic polymeric substances such as polyvinyl compounds which are compatible with the described components of the photothermographic elements of the invention. Other synthetic polymeric materials which can be employed include dispersed vinyl compounds such as in latex form and particularly those which increase dimensional stability of photographic materials. Effective polymers include water insoluble polymers of alkyl acrylates and methacrylates, acrylic acid, sulfoalkyl acrylates or methacrylates, and those which have crosslinking sites which facilitate hardening or curing as well as those which have recurring sulfobetaine units as described in Canadian Pat. No. 774,054. Useful high molecular weight materials and resins include poly(vinyl butyral), cellulose acetate butyrate, polymethylmethacrylate, ethyl cellulose, polystyrene, poly(vinyl chloride), chlorinated rubber, polyisobutylene, butadiene-styrene copolymers, vinyl chloride-vinyl acetate copolymers, copolymers of vinyl acetate, vinyl chloride and maleic acid and poly(vinyl alcohol).

A so-called development modifier, also known as a toning agent, an accelerator-toning agent, or an activator-toning agent, may be used in photothermographic elements according to the invention to obtain a desired image. The so-called development modifier is typically useful at a concentration of about 0.01 moles to about 0.1 moles of development modifier per mole of silver salt oxidizing agent in the photothermographic material according to the invention. A typical useful so-called development modifier is a heterocyclic compound containing at least one nitrogen atom described as a toning agent in Belgian Pat. No. 766,590 issued June 15, 1971. Typical development modifiers include, for example, phthalimide, N-hydroxyphthalimide, N-hydroxy-1,8-naphthalimide, N-potassium phthalimide, N-mercury phthalimide, succinimide and N-hydroxysuccinimide. Other so-called development modifiers which can be employed include 1-(2H)-phthalazinone, 2-acetyl-phthalazinone and the like. If desired, combinations of development modifiers can be employed in the described photothermographic materials.

It is believed that the described development modifiers provide increased development rate in the described photothermographic materials as well as provide improved image discrimination. In some cases the so-called development modifiers provide increased photographic speed as well as improved tone. The mechanism by which these results are provided is not fully understood.

The components of a photothermographic material according to the invention described herein can be coated on a wide variety of supports to provide a photothermographic element including those described hereinabove for radiation sensitive elements. Useful supports must be capable of withstanding the processing temperatures employed for providing a developed image.

Spectral sensitizing dyes can be used conveniently to confer additional sensitivity to photothermographic elements of the present invention. For instance, additional spectral sensitization can be obtained by treating the photographic silver halide with a solution of a sensitizing dye in an organic solvent or the dye can be added in the form of a dispersion as described in British Pat. No. 1,154,781. The spectral sensitizing dye can either be added to the photothermographic composition as a final step or at some earlier stage in preparation of the composition.

Sensitizing dyes useful in sensitizing silver halide compositions according to the invention are described, for example, in U.S. Pat. Nos. 2,526,632 (Brooker et al.), issued Oct. 24, 1950; 2,503,776 (Sprague), issued Apr. 11, 1950 and 3,384,486 (Taber et al.), issued May 21, 1968. Spectral sensitizers, which can be used, include the cyanines, merocyanines, complex (trinuclear or tetranuclear) cyanines, holopolar cyanines, styryls, hemicyanines such as enamine, hemicyanines, oxonols and hemioxonols. Dyes of the cyanine classes can contain such basic nuclei as the thiazolines, oxazolines, pyrrolines, pyridines, oxazoles, thiazoles, selenazoles and imidazoles. Such nuclei can contain alkyl, alkylene, hydroxyalkyl, sulfoalkyl, carboxyalkyl, aminoalkyl, and enamine groups that can be fused to carbocyclic or heterocyclic ring systems either unsubstituted or substituted with halogen, phenyl, alkyl, haloalkyl, cyano, or alkoxy groups. The dyes can be symmetrical or unsymmetrical and can contain alkyl, phenyl, enamine or heterocyclic substituents on the methine or polymethine chain.

The merocyanine dyes can contain the basic nuclei described, as well as acid nuclei such as thiohydantoins, rhodanines, oxazolidenediones, thiazolidenediones, barbituric acids, thiazolineones and malononitrile. These acid nuclei can be substituted with alkyl, alkylene, phenyl, carboxyalkyl, sulfoalkyl, hydroxyalkyl, alkoxyalkyl, alkylamine groups or heterocyclic nuclei. Combinations of these dyes can be used, if desired. In addition, supersensitizing addenda which do not absorb visible light may be included such as, for instance, ascorbic acid derivatives, azaindenes, cadmium salts and organic sulfonic acid as described in U.S. Pat. Nos. 2,933,390 (McFall et al.), issued Apr. 19, 1960 and 2,937,089 (Jones et al.), issued May 17, 1970.

The sensitizing dyes and other addenda used in the photothermographic materials of the invention can be added from water solutions of useful organic solvents can be used. The compounds can be added using various procedures including those, for example, described in U.S. Pat. Nos. 2,912,343 (Collins et al.), issued Nov. 10, 1959; 3,342,605 (McCrossen et al.), issued Sept. 19, 1967; 2,996,287 (Audran), issued Aug. 15, 1961 and 3,425,835 (Johnson et al.), issued Feb. 4, 1969.

A variety of color-forming couplers are useful in the photothermographic elements of the present invention. The oxidized form of the reducing agent, preferably a sulfonamidophenol reducing agent, reacts with the coupler to form a dye imagewise in the exposed photothermographic element upon overall heating. Preferred color-forming couplers include "four equivalent" color-forming couplers. Although it is appreciated that reactions in heated thermographic elements are not thoroughly understood at this time, and it is possible that the relative stoichiometry of the reactions of silver salt and color-forming coupler(s), respectively, may differ in thermographic reactions as compared with ordinary color photographic development processing, it should be understood that the term "four equivalent" as used herein with regard to color-forming coupler compounds is intended to have the same meaning as it has in such conventional color processing art; that is, it encompasses color-forming coupler compounds which are "unsubstituted" at their respective "coupling position". For example, well-known four-equivalent yellow dye-forming couplers include those compounds having an active ketomethylene structure:

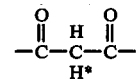

wherein the * denotes the "active" or coupling position of the coupler, or the point at which reaction of coupler with oxidized color developing material occurs to form the dye. Similarly, an example of a class of four-equivalent magenta and cyan dye-forming compounds, respectively, includes compounds having the structures:

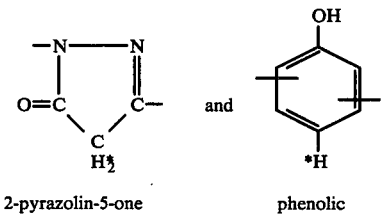

2-pyrazolin-5-one           phenolic wherein the * designates the coupling position.

Many "four-equivalent" color-forming coupling compounds are known in the art, many examples of which can be found, for example, in U.S. application Ser. No. 642,928 described hereinabove and U.S. Pat. Nos. 2,369,489; 2,875,057; 3,265,506; 2,474,293; and 2,772,162 as well as in many of the other publications referred to in Paragraph XXII "Color Materials", page 110 of Product Licensing Index, Volume 92, December 1971 published by Industrial Opportunities Ltd., Homewell, Havant Hampshire, P09 1EF, UK and on pages 822-5, Volume 5, Kirk-Othmer, "Encyclopedia of Chemical Technology" and in Glafkides "Photographic Chemistry", Volume 2, pages 596-614.

Some particularly useful four equivalent, color-forming couplers include 2-anilino-4-phenylthiazole, o-acetoacetanilide, 3-(γ-p-nitrophenylpropyl)-6-methyl-1H-pyrazolo-[3,2-c]-s-triazole, 5-[α-(2,4-di-tert-amylphenoxy)-hexamido]-2-heptafluorobutyramidophenol, 1-(2,4,6-trichlorophenyl)-3-[3-(2,4-di-tert-amyl phenoxyacetamido)benzamido]-5-pyrazolone, and α-pivalyl-2-chloro-5-[γ-(2,4-di-tert-amylphenoxyl)-butyramido]acetanilide.

In the photothermographic elements of the present invention, the concentration of each color-forming coupler used is typically within the range of from about 0.25 to about 4 moles per mole of reducing agent.

The described components of a photothermographic material can be in a variety of locations in a photothermographic element according to the invention, such as in various layers of a photothermographic element, depending upon the particular components, the desired image, processing conditions and the like. For example, the described photographic silver halide can be in a layer separate from the other components of the photothermographic material. It is often desirable, however, to employ the described components in a single layer of a photothermographic element for convenience of coating.

The photothermographic compositions can be coated on a suitable support by various coating procedures including dip coating, airknife coating, curtain coating or extrusion coating using hoppers such as described in U.S. Pat. No. 2,681,284 issued June 15, 1954. If desired, two or more layers can be coated simultaneously such as described in U.S. Pat. No. 2,761,791 (Russell), issued Sept. 4, 1956 and British Pat. No. 837,095.

Photothermographic elements according to the invention can contain photographic speed-increasing compounds, hardeners, antistatic layers, plasticizers and lubricants, coating aids, brighteners, spectral sensitizing dyes, absorbing and filtering dyes, each as described hereinabove and in the *Product Licensing Index*, Volume 92, December 1971, Publication No. 9232, pages 107–110, published by Industrial Opportunities Ltd., Homewell, Havant Hampshire, P09 1EF, UK.

A process for producing a photographic image comprises the steps of (1) exposure of an improved photothermographic element to light, said element comprising a support having thereon a layer comprising a reducing agent; a silver salt oxidizing agent; a binder; and a silver halide; and (2) thermal development at a temperature above about 80° C., the improvement comprising incorporation into the photothermographic element, a thiyl bleaching agent precursor having the formula (I) above wherein Z comprises the atoms necessary to complete a 5 to 7 member heterocyclic ring; and $R^1$ is independently selected from the group consisting of hydrogen and oxo. $R^1$ can be a complexing ligand for silver (I) ion wherein the Ksp of the complexed product of the ligand and silver (I) ion is less than about $10^{-12}$ at 25° C. when the precursor is in a layer other than the silver halide emulsion layer. Bleaching of the silver present in the photothermographic element can provide a negative dye image or a positive image in the element, depending upon the components of the photothermographic material selected.

A variety of exposure means is useful for providing a latent image in a photothermographic material as described. A latent image is typically provided by imagewise exposure to electromagnetic radiation which includes visible light. A latent image can be provided, for example, by imagewise exposure with, for instance, ultraviolet radiation, infrared radiation, a laser, electrical energy and the like. The exposure should be sufficient to provide a developable latent image in the described photothermographic material. Exposure above that which is necessary to provide a latent image can be employed if desired.

After imagewise exposure of the photothermographic material, a dye image can be developed in the photothermographic material by heating the photothermographic material to moderately elevated temperatures. A useful temperature for providing a black-and-white or a color image is within the range of about 80° C. to about 250° C. The photothermographic element is heated within the described range for a time sufficient to provide an image, typically for about 0.5 seconds. By increasing or decreasing the length of time of heating, a higher or lower temperature within the described range can be employed depending upon the desired image, the particular components of the photothermographic material and the like. A color image is typically provided within several seconds at a processing temperature of about 110° C. to about 165° C. and a black-and-white image is typically provided at a temperature of about 130° to about 180° C.

Any suitable means can be useful providing the desired processing temperature. The heating means can be a simple hot plate, iron, roller or the like.

Processing is usually carried out under ambient conditions of pressure and humidity. Conditions outside normal atmospheric pressure and humidity can be employed if desired.

The pH of a photothermographic composition useful in the photothermographic elements of the present invention can vary. In an aqueous formulation, it is typically less than about 7, such as from about 2 to about 6.

As described hereinabove for radiation sensitive elements, certain of the thiyl bleaching agent precursors may be mixed with the coating composition of the photothermographic element and coated together in the same layer as the silver halide. These precursors do not interfere with either exposure, thermal development or any color-forming reactions if their redox potentials are such that the thiyl precursor used does not oxidize the developer used. Following processing, the thiyl bleaching agent can be made to selectively bleach the silver image by introducing a suitable complexing agent for silver (I) ion. This latter agent suppresses the concentration of silver (I) ion, thereby promoting the bleaching of silver metal.

Other thiyl bleaching agent precursors cannot be incorporated directly within the light sensitive emulsion layer without possible desensitization of the layer. These agents have substituents which are complexing ligands for silver (I) ion wherein the Ksp of the complexed product of the ligand and silver (I) is greater than about $10^{-12}$ at 25° C. These thiyl compounds may be coated in interlayers or overcoats such that development is completed before they diffuse into the silver emulsion layer and initiate bleaching.

Alternatively, thiyl bleaching agent precursors and complexing agents or thiyl bleaching agent precursors having complexing ligands can be diffused into a developed photothermographic element from a second element such as an activator sheet. This is particularly advantageous when the complexing agent or ligand is not compatible with the silver halide emulsions or when bleaching of color-forming photothermographic elements by bleaching solutions disclosed herein is not practical because the image dyes are soluble in the bleaching solvent, such as methanol, and may be undesirably removed from the elements.

The activator sheet may comprise a composition comprising meltable nonreactive solid, that is a thermal solvent, such as methylanisate, hexanediol, acetamide and the like; a suitable binder, such as poly(vinyl butyral), poly(vinyl pyrrolidone) and the like; and a suitable coating solvent, such as acetone, toluene, methylethylketone, methanol and the like, said composition coated on a support such as poly(ethylene terephthalate) or resin-coated paper and the like. The meltable solid diffuses into the photothermographic element when the sheet and photothermographic element are heated while in contact, and carries the bleaching agent and/or complexing agent with it into the bleachable layers of the element.

Instead of using a separate activator sheet, one can coat the activator composition described hereinabove as an overcoat on the photothermographic element. Upon thermal development, the thermal solvent diffuses into the image layers of the element carrying with it the bleaching chemistry.

Complexing agents useful in the present invention may be generated from complexing agent precursors, such as 1,8-(3,6-dioxaoctane)-bis-isothiouronium-p-toluene-sulfonic acid (DBI) and others described in U.S. Pat. No. 3,531,285 here incorporated by reference. It is believed that these precursors slowly release complexing agents which, with the thiyl bleaching agents, bleach silver images during thermal development so that bleaching and development is accomplished in one heating step.

The following preparative methods are included to show how typical thiyl bleaching agent precursors of the present invention may be prepared.

PREPARATION 1

Synthesis of Compound 2

A mixture of 2,2,6,6-tetramethyl-4-piperidine (37 g, 0.24 mole) and N,N-dimethylformamide (100 ml) was cooled to −40° C. Sulfur dichloride (6.2 g, 0.06 mole) was added to the above mixture over a period of 30 minutes. The resulting reaction mixture was stirred an additional 30 minutes before it was carefully precipitated in stirring ice water. The resulting brown solids were collected, dried and recrystallized in hexane to give 4.5 g of Compound 2 (tan crystals, m.p. = 135°–138° C.).

PREPARATION 2

Synthesis of Compound 1

A mixture of 2,2,6,6-tetramethylpiperidine (37 g, 0.24 mole) and N,N-dimethylformamide (100 ml) was cooled to −40° C. Sulfur dichloride (6.2 g, 0.06 mole) was added to the above mixture over a period of 30 minutes. The resulting reaction mixture was stirred an additional 30 minutes before it was carefully precipitated in stirring ice water. The resulting solids were collected, dried and recrystallized in hexane to give 4.3 of Compound 1 (white crystals, m.p. = 82°–84° C.).

The following examples are included for a further understanding of the present invention. They show the use of preferred thiyl bleaching agent precursors in radiation sensitive elements.

EXAMPLE 1

Thiyl Bleaching Agent Precursors in Photothermographic Elements

Three non-aqueous, photothermographic elements, one with Compound 2 and another with Compound 1, and the third with no thiyl bleaching agent, were prepared by coating radiation sensitive layers comprising the following components on polyester film supports:

| | |
|---|---|
| 1,1'-bis-β-naphthol (developer) | 1080 mg/m² |
| Silver bromoiodide | 3.89 mmoles/m² |
| Ag⁺ as silver behenate | 3.56 mmoles/m² |
| Behenic acid | 3.56 mmoles/m² |
| Poly(vinyl butyral) | 135.0 mg/m² |

One element contained 2.70 mmoles/m² of Compound 2 and another element contained the same amount of Compound 1 and the third element contained no thiyl precursor. Samples of each of the elements were exposed through a graduated density test object and thermally developed at 115° C for 30 seconds. The silver plus yellow dye images caused by the developer were identical in all samples, indicating that no desensitization or other adverse sensitometric effects were caused by the thiyl bleaching agents.

EXAMPLE 2

Bleaching of Silver by Dry Thermographic Process

Samples of the developed photothermographic elements described in Example 1 were further processed by heating the samples at 85° C for 90 seconds while in contact with a second coating comprising:

| | |
|---|---|
| Methylanisate | 10.8 g/m² |
| Poly(vinyl butyral) | 135.0 mg/m² |
| Silver ion complexing agent having the formula | 2.70 mg/m² |

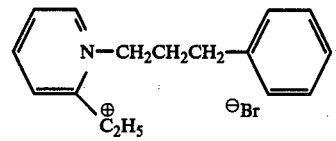

The methylanisate of the laminated coating acts as a non-reactive thermal solvent that melts below the development temperature and diffuses into the radiation sensitive photothermographic element carrying the silver ion complexing agent. This silver ion complexing agent stabilized the unexposed silver halide and activated the incorporated thiyl bleaching agents, which then oxidized the metallic silver image to a colorless product, resulting in a yellow dye image which was formed by the imagewise oxidation of the incorporated binaphthol developer. In the control coating which contained no thiyl bleaching agent precursors, the metallic silver image remained.

The invention has been described in detail with particular reference to preferred embodiments thereof, but it will be understood that variations and modifications can be effected within the scope of the invention.

What is claimed is:

1. A photothermographic element comprising a support having thereon a layer comprising:
   a. a reducing agent which provides a developed image within about 90 seconds at a temperature of about 100° to 250° C. upon heating said element;
   b. an organic silver salt oxidizing agent;
   c. a silver halide; and
   d. a thiyl bleaching agent precursor having the formula

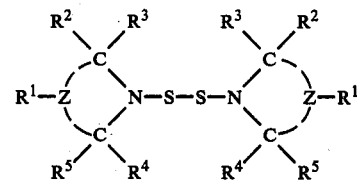

wherein Z comprises the nonmetallic atoms necessary to complete a 5 to 7 member heterocyclic ring; $R^2$, $R^3$, $R^4$ and $R^5$ are independently selected from the group consisting of alkyl, cycloalkyl, aralkyl, aryl or $R^2$ and $R^3$ or $R^4$ and $R^5$ can be taken together with the carbon atom of the ring to which they are attached to form a cycloalkyl or cycloalkenyl having from 4 to 10 carbon atoms; and $R^1$ is independently selected from the group consisting of hydrogen and oxo.

2. The photothermographic element of claim 1 wherein Z comprises the nonmetallic atoms necessary to complete a 6 member heterocyclic ring.

3. The photothermographic element of claim 2 wherein R is hydrogen.

4. The photothermographic element of claim 2 wherein R is oxo.

5. The photothermographic element of claim 1 wherein the organic silver salt oxidizing agent is a silver salt of a fatty acid.

6. The photothermographic element of claim 1 wherein the reducing agent is a sulfonamidophenol.

7. The photothermographic element of claim 1 which further comprises at least one binder.

8. The photothermographic element of claim 1 which further comprises at least one color-forming coupler.

9. A photothermographic element comprising a support having thereon a layer comprising:
   a. a reducing agent which provides a developed image within about 90 seconds at a temperature of about 100° to 250° C upon heating said element;
   b. an organic silver salt oxidizing agent; and
   c. a silver halide; and a different layer comprising a silver (I) ion complexing agent wherein the Ksp of the complexed product of silver (I) ion and the complexing agent is less than about $10^{-12}$ at 25° C; and a thiyl bleaching agent precursor having the formula

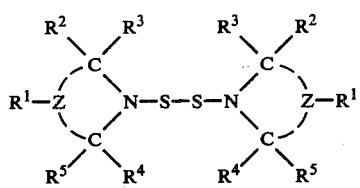

wherein Z comprises the nonmetallic atoms necessary to complete a 5 to 7 member heterocyclic ring; $R^2$, $R^3$, $R^4$ and $R^5$ are independently selected from the group consisting of alkyl, cycloalkyl, aralkyl, aryl or $R^2$ and $R^3$ or $R^4$ and $R^5$ can be taken together with the carbon atom of the ring to which they are attached to form a cycloalkyl or cycloalkenyl having from 4 to 10 carbon atoms; and $R^1$ is independently selected from the group consisting of hydrogen, oxo and a complexing ligand for silver (I) ion wherein the Ksp of the complexed product of the ligand and silver (I) is less than about $10^{-12}$ at 25° C.

10. The photothermographic element of claim 9 wherein Z comprises the nonmetallic atoms necessary to complete a 6 member heterocyclic ring.

11. The photothermographic element of claim 10 wherein R is hydrogen.

12. The photothermographic element of claim 10 wherein R is oxo.

13. The photothermographic element of claim 10 wherein R is the complexing ligand

14. The photothermographic element of claim 9 wherein the organic silver salt oxidizing agent is a silver salt of a fatty acid.

15. The photothermographic element of claim 9 wherein the reducing agent is a sulfonamidophenol.

16. The photothermographic element of claim 9 which further comprises at least one binder.

17. The photothermographic element of claim 9 which further comprises at least one color-forming coupler.

18. The photothermographic element of claim 9 wherein the complexing agent is an onium halide.

19. A photothermographic element comprising a support having thereon a layer comprising:
   a. a sulfonamidophenol reducing agent;
   b. a silver behenate-behenic acid dispersion;
   c. a silver bromoiodide;
   d. a poly(vinyl butyral) binder; and
   e. at least one color-forming coupler; and another layer comprising a silver (I) ion complexing onium halide; and in the same or different layer, a thiyl bleaching agent precursor selected from the group consisting of

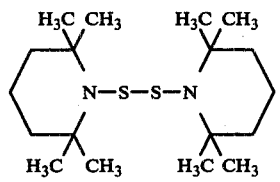

and

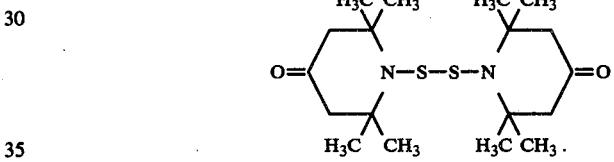

20. In a process for producing a photographic image comprising the steps of (1) exposure of a photothermographic element to light, said element comprising a support having thereon a layer comprising a reducing agent which provides a developed image within about 90 seconds at a temperature of about 100° to 250° C upon heating said element; an organic silver salt oxidizing agent; and a silver halide; and (2) thermal development at a temperature above about 80° C, the improvement comprising incorporation into the photothermographic element of a thiyl bleaching agent precursor having the formula

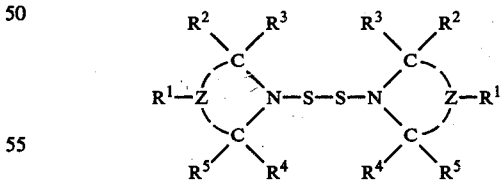

wherein Z comprises the nonmetallic atoms necessary to complete a 5 to 7 member heterocyclic ring; $R^2$, $R^3$, $R^4$ and $R^5$ are independently selected from the group consisting of alkyl, cycloalkyl, aralkyl, aryl or $R^2$ and $R^3$ or $R^4$ and $R^5$ can be taken together with the carbon atom of the ring to which they are attached to form a cycloalkyl or cycloalkenyl having from 4 to 10 carbon atoms; and $R^1$ is independently selected from the group consisting of hydrogen and oxo.

* * * * *

UNITED STATES PATENT AND TRADEMARK OFFICE
CERTIFICATE OF CORRECTION

PATENT NO. : 4,124,398

DATED : November 7, 1978

INVENTOR(S) : Samuel J. Ciurca, Jr., and Carl F. Kohrt

It is certified that error appears in the above-identified patent and that said Letters Patent are hereby corrected as shown below:

Column 22, line 19, in the formula, "⊕" should be under the "N". Column 23, line 5, "R" should read --$R^1$--; line 7, "R" should read --$R^1$--; lines 24-29, "and a different....formula" should be a separate paragraph flush with the left margin; line 55, "R" should read --$R^1$--; line 57, "R" should read --$R^1$--; line 59, "R" should read --$R^1$--. Column 24, lines 16-20, "and another....consisting of" should be a separate paragraph flush with the left margin.

Signed and Sealed this

Seventeenth Day of April 1979

[SEAL]

Attest:

RUTH C. MASON
Attesting Officer

DONALD W. BANNER
Commissioner of Patents and Trademarks